United States Patent [19]

Lai et al.

[11] Patent Number: 4,857,649
[45] Date of Patent: Aug. 15, 1989

[54] AZOLE DERIVATIVES OF NAPHTHALENONE OXIME ESTERS

[75] Inventors: Hoi K. Lai, Guelph, Canada; Robert A. Davis; Allen R. Blem, both of Cheshire, Conn.

[73] Assignees: Uniroyal Chemical Company, Inc., Middlebury, Conn.; Uniroyal Chemical LTD/LTEE, Don Mills, Canada

[21] Appl. No.: 223,054

[22] Filed: Jul. 21, 1988

[51] Int. Cl.$^4$ ............... C07D 249/08; A01N 43/653
[52] U.S. Cl. ..................... 548/262; 514/383; 71/92
[58] Field of Search ............ 548/262, 265; 71/92; 514/383

[56] References Cited

U.S. PATENT DOCUMENTS 4,309,434  1/1982  Kramer et al. ............... 424/269
4,377,697  3/1983  Fellner et al. ............... 548/346
4,599,348  7/1986  Schmetzer et al. ............ 514/383

FOREIGN PATENT DOCUMENTS 146047   6/1985  European Pat. Off. .
3244985  7/1984  German Democratic Rep. .

OTHER PUBLICATIONS

*Journal of Medicinal Chemistry*, vol. 12, No. 5, Sep. 1969, pp. 784–791.

*Primary Examiner*—Richard L. Raymond
*Assistant Examiner*—Peter G. O'Sullivan
*Attorney, Agent, or Firm*—Raymond D. Thompson

[57] ABSTRACT

The invention relates to compounds useful as fungicides and plant growth regulants represented by the formula

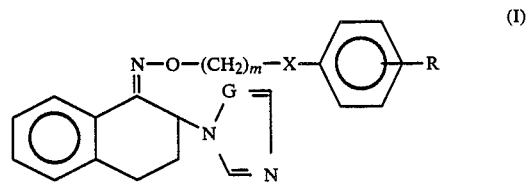

(I)

in which:
R is a substituent or a group of substituents representing halogen, lower alkyl of 1 to 6 carbon atoms, phenyl, substituted phenyl, phenoxy, substituted phenoxy, naphthyl, nitro, cyano, lower alkoxy, alkoxycarbonyl, or trifluoromethyl;
X is single bond, oxygen, sulfur or sulfonyl;
G is CH or nitrogen atom;
m is an integer from 1 to 4 and a process of making the compound.

8 Claims, No Drawings

AZOLE DERIVATIVES OF NAPHTHALENONE OXIME ESTERS

BACKGROUND OF THE INVENTION

1. Field of the Invention

The present invention is directed to a new class of oxime derivatives of α-azolyl naphthalenones. More specifically, the present invention is directed to a new class of oxime derivatives of α-azolyl naphthalenones useful as fungicides and plant growth regulants.

2. Background of the Prior Art

The control of phytopathogenic fungi is of great economic importance since fungal growth on plants or on parts of plants, i.e., fruits, blossoms, foliage, stems, tubers, roots, inhibits production of foliage, fruit or seed and the overall quality of the harvested crop.

Obviously, fungicides are well known in the art. However, the continuous economic toll, discussed above, taken by fungi establish a continuing need to develop new, more effective fungicides which possess curative, preventative and systemic action to protect cultivated plants. Those requirements must be accomplished without any adverse side effects, caused by the fungicide, on the plants to be protected.

Another need in the art is the continual requirement to develop new and effective plant growth regulants. As in the case of fungicides, there is a continuing need in the art to develop new and better plant growth regulants which regulate the growth of plants. It will be understood that the term plant as used herein includes plant parts such as foliage, roots, flowers, stems and seeds. Depending on crop, variety, dosage, time of application and certain cultural practices, growth regulating effects which may be obtained include one or more of the following: dwarfing, cessation of terminal growth, inhibition or stimulation of axillary and intercalary growth, retardation or stimulation of internode elongation, inhibition or stimulation of flowering or reproductive development, and the like. Especially desirable are plant growth regulants that retard or inhibit undesirable growth, such as excess foliage, stems, branches, etc., of important crops without adversely affecting the yield and quality of the commercial crop to be harvested.

U.S. Pat. No. 4,309,434 describes a-phenyl-1-oximins-2-(1,2,4-triazol-1-yl)-ethanes which possess fungicidal properties. The oximins-triazolyl-ethanes of '434 are structurally distinguished from the oxime derivatives of α-azolyl naphthalenones.

U.S. Pat. No. 4,377,697 is directed to a class of imidazole hydrazone and hydrazine derivatives. These compounds are also structurally distinguished from the instant invention. The compounds of this disclosure are described as possessing anti-anaerobe and anti-fungal activity.

Azolylacetophenone oxime ether compounds are disclosed in both Ger. Offen. DE No. 3,244,985 EP No. 113,839 and Ger. Offen. DE No. 3,343,415 EP No. 146,047. These compounds are recited to possess fungicidal activity and plant growth regulation. These compounds differ structurally from the oxime derivatives of α-azolyl naphthalenones in that the triazolyl group is not attached to a cyclic ring as is the case of the instant invention.

The above remarks establish the need in the art for new and improved fungicides and plant-growth regulants. The above discussion, furthermore, emphasizes the uniqueness of oxime derivatives of naphthalenone compounds. Such compounds are not only not disclosed in the art, but no teaching of their use as fungicides or plant-growth regulants is made.

BRIEF DESCRIPTION OF INVENTION

This invention relates to novel oxime derivatives of α-azolyl naphthalenones useful as fungicides and plant growth regulants and can be represented by formula (I).

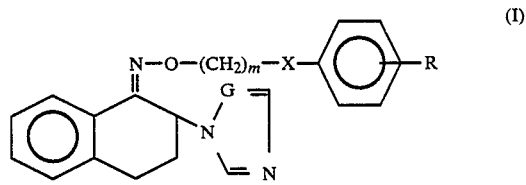

in which:

R is a substituent or a group of substituents representing halogen, lower alkyl of 1 to 6 carbon atoms, phenyl, optionally substituted phenyl, phenoxy, optionally substituted phenoxy, naphthyl, nitro, cyano, low or alkoxy, alkoxycarbonyl, or trifluoromethyl;

X is single bond, oxygen, sulfur or sulfonyl;

G is CH or nitrogen atom;

m is an integer from 1 to 4.

Compounds of formula (I) are prepared by reacting an oxime azole (II) with a halide (III) in an inert hydrocarbon solvent such as toluene, xylene, benzene or chlorobenzene with vigorous stirring in the presence of a phase transfer catalyst and either a powdered metal hydroxide—preferably sodium hydroxide or potassium hydroxide—or a concentrated aqueous solution of the same. The reaction is carried out at a temperature ranging from ambient temperature to refluxing temperature of the solvent. In the cases of bromide (III,Y=Br), the ambient temperature is preferred. In the cases of a less reactive chloride (III,Y=Cl), the refluxing temperature is preferred.

Suitable phase transfer catalysts are for example trialkylbenzylammonium or tetraalkylammonium halides preferably with 4 to 12 carbon atoms in the alkyl radical.

In carrying out the process according to the invention, 1 to 1.5 equivalent of halide (III) is preferably employed per mole of the oxime azole of formula (II). In order to isolate the product of formula (I), the reaction mixture is freed from the reaction medium, and water and an organic solvent are added to the residue. The organic phase is separated off and worked up in the conventional manner.

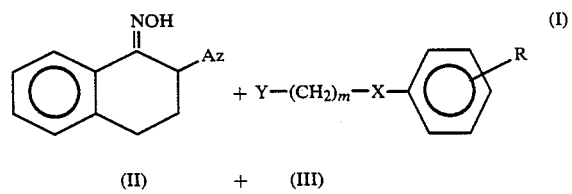

Az=1,2,4-triazole, imidazole
Y=Cl, Br
X, R and m as previously defined.

Compounds of structure (I) form salts with organic and inorganic acids. These salts can be obtained in a simple manner by common salt formation methods, for example by dissolving a compound of formula (I) in a suitable inert solvent and adding the acid. Diethylether and toluene are two common solvents. The resulting salts can be isolated in any conventional manner, such as by filtration and, if appropriate, purifying by washing with an inert organic solvent. The physiologically acceptable salts are also intended to be within the scope of this invention.

It should be noted that compounds of structure (I) may exist as syn and anti isomeric mixture. Such isomers are not necessarily separated and their mixture are also intended to be within the scope of this invention.

More preferably, the compounds in this invention have structures represented by formula (I).

where
R is a substituent or a group of substituents representing halogen, nitro, cyano, lower alkoxy or trifluoromethyl;
X is single bond
G is CH or nitrogen atom
m is an interger from 1 to 4

The compounds having the structural formula (I) are useful in a process for controlling phytopathogenic fungi. In this process a fungicidally effective amount of the compound having a structural formula (I) in which:

R is a substituent or a group of substituents representing hydrogen, halogen, lower alkyl of 1 to 6 carbon atoms, phenyl, optionally substituted phenyl, phenoxy, optionally substituted phenoxy, naphthyl, nitro, cyano, lower alkoxy, alkoxycarbonyl, or trifluromethyl;
X is single bond, oxygen, sulfur or sulfonyl;
G is CH or nitrogen atom;
m is an integer from 1 to 4 is applied to the locus under attack by said fungi.

More preferably, the process for controlling fungi comprises applying a fungicidally effective amount of the compound having the structural formula (I) where R is a substituent or a group of substituents representing halogen, nitro, cyano, lower alkoxy or trifluoromethyl;
X is a single bond
G is CH or nitrogen atom
m is an integer from 1 to 4 to the locus under attack by said fungi.

In a first preferred embodiment, the method by which a fungicidally effective amount of the compound having structural formula (I) is applied to the plants to be protected from phytopathogenic fungi is by application of the compound having the structural formula (I) to the foliage of the plants to be protected. This compound is applied to the foliage in a concentration of 0.125 to 10 kilograms per hectare (kg/ha). More preferably, the embodiment wherein fungi are controlled in a process comprising applying a fungicidally effective amount of the compound having structural formula (I) entails applying 0.125 to 5.0 kg/ha of compound (I) to the foliage of the plants to be protected from said phytopathogenic fungi.

The oxime azoles of formula (II) are novel and can be prepared by reacting an azole ketone (IV) with hydroxylamine in an alcoholic solvent, preferably ethanol, at temperatures between 20° C. and 80° C., preferably at reflux temperature. The hydroxyalamine is preferably employed in the form of its hydrochloride salt (V) in the presence of an acid-binding agent such as pyridine.

a. Az=imidazole
b. Az=1,2,4-triazole Imidazole ketone (IV a) is known (Chemical Abstract Registry No. [84391-39-9] whereas triazole (IV b) is novel and may be prepared by reaction of the bromoketone (VI) (Chemical Abstract Registry No. [13672-07-6] with 1,2,4-triazole by methods disclosed by P. A. J. Janssen et al, in J. Med. Chem. 1969, 12, 784, whose disclosure is incorporated herein by reference.

Organic halides of formula (III) are generally known in the literature and can be prepared by those skilled in the art.

In the second preferred embodiment of the process for controlling phytopathogenic fungi, a fungicidally effect amount of the compound having the structural formula (I) is applied to the soil in which the plants to be protected from phytopathogenic fungi are grown. In this embodiment, the compound having the structural formula (I) is applied to the soil in which the plants to be protected are grown at a concentration of 10 to 500 mg/l. The exact dosage, within this concentration range, is dictated by the fungi to be controlled and the particular plants to be protected.

As those skilled in the art are aware, the first preferred embodiment of the process for controlling fungi is the foliage method. The second preferred embodiment is the systemic method of application. Either method may be utilized prior to infection or after fungi attack has begun.

Alternately, in yet another embodiment of the process of the present invention for controlling phytopathogenic fungi, the compound having the structural formula (I) may be applied to the seeds as a coating. This method provides plant protection from dangerous fungi by either chemotherapeutic means or systemic means or both. That is, the coating to the seed may protect the soil from infection by the fungi or may be taken up by the plant systemically to protect the plant from the fungal attack. In this seed coating method, the appropriate concentration of the compound having the structural formula (I) is in the range of between 5 and 75 grams of compound per 100 kg. of seed.

In still another aspect of the present invention, a process for regulating growth of a plant is provided. In this process a plant growth regulant effective amount of the compound having structural formula (I), where R, X, G and m have the meanings given for compound (I), is applied to the plant whose growth is to be regulated.

As a plant growth regulant, the preferred compounds are those where R is hydrogen or a halogen, X is a single bond or oxygen, G is nitrogen or CH and m is 1 to 4. More preferable compounds are those in which R is H, Cl or Br, X is a single bond, G is nitrogen, and m is 1 or 2.

Yet another important aspect of the present invention involves the disclosure of new fungicidal compositions. The fungicidal composition of the present invention comprises a fungicidally effective amount of the compound having the structural formula (I), where R, X, G and m have the meanings given for compouad (I), and a carrier therefor.

More preferably, the fungicidal composition comprises a fungicidally effective amount of the compound having structural formula (I), wherein the meanings of R, X, G and m have the preferred meanings for the compound having structural formula (I), and a carrier therefor.

In a final aspect of the present application a plant growth regulant composition is provided. This composition comprises a plant growth regulant effective amount of the compound having the structural formula (I), where R, X, G and m have the meanings given for compound (I), and a carrier therefor.

More preferably, a plant growth regulant composition is disclosed which comprises a plant growth regulant effective amount of the compound having structural formula (I) wherein the preferred meanings of R, X, G and m are those given for the preferred embodiment of the compound having structural formula (I), and a carrier therefor.

The carrier employed in the fungicidal and plant growth regulant compositions may be a finely divided or granular organic or inorganic inert material. Among the inert carriers within the contemplation of this invention are attapulgate clay, sand, vermiculite, corncobs, activated carbon and mineral silicates such as mica, talc, pyrophyllite and clays.

In another preferred embodiment of carrier employed in the composition of this invention, the carrier comprises a solution. That is, the active agent, a compound whose structural formula is (I) is dissolved in a suitable solvent which acts as the carrier. Among the solvents, acting as carrier, within the contemplation of this invention are acetone, methanol, isopropanol, t-butyl alcohol, cyclohexanol, n-butyl alcohol, cyclohexanone, toluene, xylene, dioxane, dimethylformamide, dimethylsulfoxide, ethylene dichloride, diacetone alcohol, and N-methylpyrrolidone.

In still another preferred embodiment of the carrier utilized in the composition of the present invention, the carrier comprises a water emulsion. The water emulsion is prepared from a solution as described immediately above. To the solution is added a surface active agent. Surface active agents suitable for use in forming the emulsion of this invention are known to those skilled in the art. *McCutcheon's Detergents and Emulsifiers,* Allured Publishing Corp., Ridgewood, New Jersey (1970); U.S. Pat. Nos. 2,514,916, Columns 2 to 4; and 2,547,734, Columns 3 and 4, provide detailed examples of such surface active agents. The surface active agents may be anionic, non-ionic or cationic.

In still another embodiment of a carrier used in the composition of the present invention, the carrier is a dispersant. In this embodiment, the active agent, the compound having structural formula (I), is mixed with a dispersant. The dispersant includes a solvent of the type described above, one of the above-described surface active agents and water. The active agent is dissolved in the solvent to form a solution. The solvent is dispersed in the water with the aid of the surface active agent.

In still another embodiment of the carrier constituent of the composition of the present invention, the active compound, the compound having the structural formula (I), is premixed with an inert solid carrier which is added to a surface active agent and water to provide another form of dispersion type carrier within the contemplation of the composition of this invention.

The embodiment discussed immediately above, the disposal of the compound having the structural formula (I) on a solid inert carrier which is dispersed in the liquid to form a dispersion, may alternatively be employed in a non-liquid form. That is, the composition of this invention may take the form of dust, granules or a paste of a wettable powder. In these embodiments the active compound of this invention, the compound having the structural formula (I), is admixed with an inert solid carrier to form a solid composition. Thus, for example, in the embodiment wherein a powder is formed, the solid inert carrier is provided in powder form. In many such cases the inert carrier is a mineral silicate. The solid may be made wettable by the addition of a surface active agent, well known to those skilled in the art, and referred to in the above-recited references directed to surface active agents.

In a final embodiment of the carrier component of the composition of this invention, the carrier is an aerosol. To prepare an aerosol, the active compound is dissolved in a first solvent. This first solvent is conventional in the sense that although it is volatile it is not highly volatile.

This solution is then admixed with a highly volatile solvent, a so-called liquid aerosol carrier. The aerosol carrier is liquid only under elevated pressure. At ordinary temperatures and at atmospheric pressure, the aerosol carrier is a gas. In a subembodiment of this preferred carrier, the aerosol carrier may itself be active. For example, the carrier may be an insecticide, a herbicide, a bactericide or the like.

Among the carriers discussed above, the carriers comprising solvents and emulsions are particularly preferred in the production of the fungicidal and plant growth regulant compositions of the present invention.

The following examples are given to illustrate the scope of the present invention. Because these examples are given for illustrative purposes only, the invention embodied herein should not be limited to the actual examples provided.

EXAMPLE 1

Preparation of 3,4-Dihydro-2-[1H-1,2,4-triazol)-1-yl)]-1(2H)-naphthalenone

To a mixture of 15 g 1,2,4-triazole, 30 g potassium carbonate and 250 ml acetonitrile at 45° C. was added a solution of 45 g 2-bromo-3,4-dihydro-1(2H)-naphtalenone in 150 ml acetonitrile over 2 hours. The mixture was kept at 45° C. for 5 hours, then brought to gentle reflux for 4 hours. The solid was filtered off, the filtrate evaporated to dryness and the residue taken up in methylene chloride. This was then washed with water, dried over sodium sulfate and evaporated to give a light brown solid. Recrystallization from toluene yielded 42 g of the titled compound, m.p.=96°–98° C.

EXAMPLE 2

Preparation of 3,4-Dihydro-2-[1H-(1,2,4-triazol)-1-yl]-1 (2H)-naphthalenone; Oxime A mixture of 16.3 g 3,4-dihydro-2-[1H-(1,2,4-triazol)-1-yl]-1(2H)-naphthalenone, 5.8 g hydroxylamine hydrochloride, 6.7 g pyridine and 100 ml absolute ethanol was refluxed for 2 hours, then cooled and poured slowly into 300 ml of ice-cold water. The resulting precipitae, was collected, filtered and washed with n-hexane to give 13.5 g of the titled oxime, m.p.=185°–186° C.

EXAMPLE 3

Preparation of 3,4-Dihydro-2-[1H-(1,2,4-triazole)-1-yl]-1(2H)-naphthalenone,O-[(2-bromophenyl)methyl]oxime (Compound No. 37)

To a mixture of 1.45 g 3,4-dihydro-2-[1H2,4-triazol)-1-yl]-1(2H)-naphthalenone oxime, 1 g triethylbenzylammonium bromide, 100 ml of 25% aqueous sodium hydroxide and 100 ml toluene at room temperature was added, over 20 minutes, 1.6 g of 2-bromobenzyl bromide. The mixture was stirred for 16 hours, then filtered and the organic phase separated. The aqueous phase was extracted with toluene and the combined organic phase washed with water and dried over sodium sulfate. Upon work-up 2.5 g of the titled compound was obtained as a yellow oil. NMR (CDCl$_3$)δ: 6.9–8.2(10H,m), 6.0(1H,t), 5.26(2H,S), 1.8–2.9(4H,m).

EXAMPLE 4

Preparation of 3,4-Dihydro-2-[(1H-imidazol)-1-yl]-1(2H)-napthalenone-, O-[(4-fluorophenyl)methyl]oxime (Compound No. 22)

In a manner analogous to the preparation of Example 3, 2.9 g of 3,4-dihydro-2-[(1H-imidazol)-1-yl[-1(2H)-napthalenone oxime was reacted with 2.5 g of 4-fluorobenzyl bromide in the presence of 1 g tetrapentylammonium iodide to give 4.8 g of the titled oxime ether as an oil. NMR (CDCl$_3$)δ:8.1(1H,m), 6.7–7.5(10H,m), 5.75(1H,t), 5.1(2H,S), 2.5–2.8(2H,m), 1.9–2.3(2H,m).

EXAMPLE 5

Preparation of 3,4-Dihydro-2-[1H-imidazol)-1-yl]-1(2H)-naphthalenone-, O- [4-(trifluoromethyl)phenyl]methyl oxime (Compound No. 47)

A mixture of 3 g 3,4-dihydro-2-[(1H-imidazol)-1-yl]-naphthalenone oxime, 2.6 g 4-(trifluoromethyl)benzyl chloride, 1 g tetrabutylammonium iodide, 100 ml of 25% aqueous sodium hydroxide and 100 ml toluene was refluxed for 7 hours. The reaction mixture was worked up as previously described to give 3.9 g of the titled oxime ether. NMR (CDCl$_3$)δ:8.05(1H,m), 6.8–7.7(10H,m), 5.8(1H,t), 5.2(2H,S), 2.5–2.8(2H,m), 2.0–2.5(2H,m).

EXAMPLE 6

Preparation of 3,4-Dihydro-2-[(1H-1,2,4-triazol)-1-yl]-1-(2H)-naphthalenone-,O-[-4-(chlorophenoxy)butyl]oxime (Compound No. 21)

To a mixture of 3 g 3,4-dihydro-2-[1H,1,2,4-triazol)-1-yl]-1(2H)-naphthalenone oxime, 1.2 g powdered potassium hydroxide and 0.9 g benzyltriethylammonium bromide in 30 ml toluene was added 3.6 g of 4-(chlorophenoxy)-1-bromobutane. The reaction mixture was stirred at 80°–100° C. for 2 hours. The toluene layer was washed with water; then dried (sodium sulfate) and worked up to give 5.3 g of a light brown oil. NMR (CDCl$_3$)δ:7.8–8.2(3H,m), 6.7–7.4(7H,m), 5.9(1H,t), 4.2(2H, broad t), 3.8(2H, broad t), 2.5–2.9(2H,m), 2.25–2.5(2H,m), 1.4–2.1(4H,m).

EXAMPLE 7

Preparation of 3,4-Dihydro-2-[2H-imidazol)-1-yl]-1(2H)-naphthalenone-,O-[3-phenoxyphenyl)methyl]oxime (Compound No. 66)

In a manner analogous to the preparation of Example 5, 3 g of 3,4-dihydro-2-[(1H,imidazol)-1-yl]-1(2H)-naphthalenone oxime was recated with 2.g of 3-phenoxybenzyl chloride in the presence of 1 g tetrabutylammonium iodide to give 4 g of the tilted oxime ether. NMR (CDCl$_3$)δ:8.05 (1H,m), 6.7–7.5(15H,m), 5.8(1H,t), 5.1 (2H,S), 2.55–2.8 (2H,m), 1.9–2.4(2H,m).

EXAMPLE 8

Preparation of 3,4-Dihydro-2-[(1H-1,2,4-triazol)-1-yl]-1-(2H)-naphthalenone-,O-[3-[[4-1,1-dimethylethyl)-2-methylphenyl]thio]propyl]oxime (Compound No. 45)

In a manner analogous to the preparaton of Example 3, 3 g of 3,4-dihydro-2-[(1H-12,4-triazol)-1-yl]-3-[[4-tertbutyl)-2-methylphenyl]thio]propyl bromide in the presence of 1 g tetrabutylammonium iodide to give 5 g of the titled oxime ether as an oil. NMR ((CDCl$_3$)δ:7.9–8.2(2H,m), 7.0–7.4(7H,m), 5.9(1H, broad t), 4.25(2H,t), 2.65–3.1(4H,m), 2.4(3H,S), 1.8–2.2(4H,m), 1.3(9H,S).

EXAMPLE 9

Preparation of
3,4-Dihydro-2-[1H-imidazol)-1-yl]-1(2H)-naphthalenone,-O-[(4-fluorophenyl)methyl]oxime, hydrochloride (Compound No. 33)

A solution of 1 g 3,4-dihydro-2-[(1H-imidazol)-1-yl](2H)-naphthalenone, O-[(4-fluorophenyl)methyl]oxime in 100 ml of diethyl ethyl was treated with a steady stream of hydrogen chloride gas until precipitation of salt ceased. The precipitate was collected by filtration and air-dried to yield 1 g of white solid, m.p.=171°–174° C.

EXAMPLE 10

Preparation of
3,4-dihydro-2-[1H-1,2,4-triazol)-1-yl]1(2H)-naphthalenone,-O-[2-fluorophenyl)methyl]oxime,sulfate (Compound No. 39)

A solution of 1.3 g concentrated sulfuric acid was added dropwise to a solution of 4.4 g 3,4-dihydro-2-[1H-1,2,3-triazol)-1-yl]-,O-[(2-chlorophenyl)methyl]oxime in 100 ml of toluene at 0° C. The solid settlement was collected by decantation, then triturated with methylene chloride-diethyl ether mixed solvent. Trituration was repeated once more with fresh solvent. The resulting solid was collected by filtration and air-dried to give 3.5 g of the titled sulfate, m.p.=104°–110° C.

EXAMPLE 11

Preparation of Compound Nos. 1–20, 23–32, 34–36, 38, 40–44, 46, 48–65 and 67–81

Compound Nos. 1–20, 23–32, 34–36, 38, 40–44, 46, 48–65 and 67–73 were prepared in accordance with the procedures enumerated in Example 1–10. These compounds are tabulated in Table I. Table I defines the compounds and characterizes them either by their melting point or by nuclear magnetic resonance (NMR) data. Compounds 37, 22, 47, 21, 66, 45, 33 and 39 prepared in accordance with the procedures of Example 1–10, respectively, are included in the table for completeness. The following abbreviations and symbols are used to express the NMR data in Table I: s=singlet; t=triplet; q=quartet; d=doublet; m=multiplet σ=ppm relative to TMS and H=proton.

TABLE I

| Cpd No. | R | X | m | G | Melting Point (°C.) or NMR (delta, CDCl$_3$ |
|---|---|---|---|---|---|
| 1 | H | 0 | 2 | N | 8.5 (1H,s), 7.9 (1H,s), 7.75–8.1 (1H,m), 6.7–7.5 (8H,m), 6.05 (1H,t), 4.0–4.5 (broad t + t), 2.7 (2H,m), 2.2 (2H,m). |
| 2 | H | 0 | 3 | N | 8.1 (1H,m), 7.95 (1H,s), 7.9 (1H,s), 6.75–7.45 (8H,m), 5.9 (1H,t), 4.35 (2H,t), 3.9 (3H,t) 2.7 (2H,m), 2.4 (2H,m), 2.1 (2H,m). |
| 3 | H | 0 | 4 | N | 8.15 (1H,m), 8.0 (1H,s), 7.95 (1H,s), 6.75–7.5 (8H,m), 5.95 (1H,t), 4.3 (2H,m), 3.9 (2H,m), 2.7 (2H,m), 2.1–2.6 (2H,m), 1.55–2.0 (4H,m). |
| 4 | H | Single Bond | 1 | CH (HNO$_3$) | MP = 105–108° C. |
| 5 | H | Single Bond | 1 | CH | 8.1 (1H,m), 7.0–7.5 10H,m), 6.8 (1H, broad s), 5.8 (1H,t), 5.15 (2H,s), 2.7 (2H,m), 2.2 (2H,m). |
| 6 | H | Single bond | 1 | N | 8.1 (1H,m), 7.9 (1H,s), 7.85 (1H,s), 6.9–7.4 (8H,m), 5.9 (1H, broad t) 5.1 (2H,s), 2.5 (2H,M), 2.3(2H,m). |
| 7 | 2-Cl | Single bond | 1 | N | 8.1 (1h,m), 7.9 (1H,s), 7.85 (1H,s), 6.9–7.4 (7H,m), 6.0 (1H, broad t), 5.2 (2H,s), 2.65 (2H,m), 2.3 (2H,m). |
| 8 | 3-Cl | Single bond | 1 | N | 8.0 (2H,m), 7.9 (1H,s), 6.9–7.4 (7H,m), 5.95 (1H, broad t), 5.1 (2H,s), 2.6 (2H,m), 2.3 (2H,m). |
| 9 | 4-Cl | Single bond | 1 | CH | 8.0 (1H,m), 6.95–7.5 (9H,m), 6.75 (1H,s), 5.75 (1H,t), 5.1 (2H,s), 2.6 (2H,m), 2.2 (2H,m). |
| 10 | 3-Cl | Single bond | 1 | CH | 8.0 (1H,m), 6.9–7.5 (9H,m), 6.8 (1H,s), 5.8 (1H,t), 5.1 (2H,s), 2.65 (2H,m), 2.2 (2H,m). |
| 11 | 2-Cl | Single bond | 1 | CH | 8.05 (1H,m), 7.0–7.5 (9H,m), 6.8 (1H,s), 5.85 (1H,t), 5.25 (2H,s), 2.65 (2H,m), 2.15 (2H,m). |
| 12 | H | 0 | 2 | CH | 8.05 (1H,m), 6.8–7.5 (H,m), 6.75 (1H,s), 5.7 (1H,t), 4.4 (2H,m), 4.1 (2H,m), 2.65 (2H,m), 2.15 (2H,m). |
| 13 | H | 0 | 3 | CH | 8.0 (1H,m), 6.75–7.5 (11H,m), 5.7 (1H,t), 4.3 (2H,t), 3.8 (2H,t) 2.6 (2H,m), 1.8–2.4 (4H,m). |

TABLE I-continued

| Cpd No. | R | X | m | G | Melting Point (°C.) or NMR (delta, CDCl₃) |
|---|---|---|---|---|---|
| 14 | H | O | 4 | CH | 8.0 (1H,m), 6.7–7.4 (11H,m), 5.7 (1H, broad t), 4.2 (2H,m), 3.8 (2H,m), 2.6 (2H,m), 2.1 (2H,m), 1.5–2.0 (4H,m). |
| 15 | 4-Cl | O | 2 | CH | 8.1 (1H,m), 6.7–7.5 (10H,m), 5.75 (1H,t), 4.4 (2H, broad t), 4.15 (2H, broad t), 2.75 (2H,m), 2.25 (2H,m). |
| 16 | 4-Cl | O | 3 | CH | 8.1(1H,m), 6.65–7.5 (10H,m), 5.75 (1H,t), 4.3 (2H,t), 3.7 (2H,t), 2.7 (2H,m), 1.7–2.4 (4H,m). |
| 17 | 4-Cl | O | 4 | CH | 8.1 (1H,m), 6.65–7.4 (10H,m), 5.75 (1H,t), 4.2 (2H, broad t), 3.8 (2H, broad t), 2.65 (2H,m), 2.2 (1H,m), 1.4–1.9 (4H,m). |
| 18 | 4-Cl | O | 1 | N | 7.8–8.2 (2H,m), 7.9 (1H,s), 6.9–7.5 (7H,m), 5.9 (1H, broad t), 5.1 (2H,s), 2.65 (2H,m), 1.8–2.45 (2H,m). |
| 19 | 4-Cl | O | 2 | N | 8.0 (1H,m), 7.95 (1H,s), 7.85 (1H,s), 6.7–7.4 (7H,m), 5.9 (1H, broad t), 2.45 (2H,m), 4.15 (2H,t), 2.7 (2H,m), 1.8–2.45 (2H,m). |
| 20 | 4-Cl | O | 3 | N | 8.0 (1H,m), 7.95 (1H,s), 7.85 (1H,s), 6.65–7.4 (7H,m), 5.9 (1H,t), 4.3 (2H,t), 3.75 (2H,t), 2.65 (2H,m), 2.3 (2H,m), 2.0 (2H,m). |
| 21 | 4-Cl | O | 4 | N | 7.8–8.2 (3H,m), 6.7–7.4 (7H,m), 5.9 (1H,t), 4.2 (2H, broad t), 3.8 (2H, broad t), 2.5–2.9 (2H,m), 2.25–2.5 (2H,m), 1.4–2.1 (4H,m). |
| 22 | 4-F | Single bond | 1 | CH | 8.1 (1H,m), 6.7–7.5 (10H,m), 5.75(1H,t), 5.1 (2H,S), 2.5–2.8 (2H,m), 1.9–2.3 (2H,m). |
| 23 | 4-F | Single bond | 1 | N | 8.1 (1H,m), 7.9 (1H,s), 7.85 (1H,s), 6.8–7.5 (7H,m), 5.95 (1H,t), 5.1 (2H,s), 2.7 (2H,m), 1.9–2.5(2H,m). |
| 24 | 2-F | Single bond | 1 | CH | 8.1 (1H,m), 6.8–7.5 (10H,m), 5.9 (1H,t), 5.3 (2H,s), 2.75 (2H,m), 2.25 (2H,m). |
| 25 | 2-F | Single bond | 1 | N | 8.05 (1H,m), 7.85 (2H,s + s), 6.8–7.5 (7H,m), 5.95 (1H,t), 5.2 (2H,s), 7.7 (2H,m), 2.7 (2H,m), 1.9 (2H,m). |
| 26 | 3-F | Single bond | 1 | CH | 8.1 (1H,m), 6.8–7.5 (10H,m), 5.9 (1H,t), 5.2 (2H,s), 2.8 (2H,m), 2.3 (2H,m). |
| 27 | 3-F | Single bond | 1 | N | 8.05 (1H,m), 7.92 (1H,s), 7.9 (1H,s), 6.8–7.5 (7H,m), 6.0 (1H,t), 5.15 (2H,s), 2.75 (2H,m), 1.9–2.6 (2H,m). |
| 28 | 4-Br | Single bond | 1 | CH | 8.0 (1H,m), 6.75–7.5 (10H,m), 5.8 (1H,t), 5.1 (2H,s), 2.7 (2H,m), 2.2 (2H,m). |
| 29 | 4-Br | Single bond | 1 | N | 8.05 (1H,m), 7.94 (1H,s), 7.9 (1H,s), 7.0–7.5 (7H,m), 5.98 (1H,t), 5.1 (2H,s), 2.75 (2H,m), 2.0–2.6 (2H,m). |
| 30 | 4-Br | Single bond | 1 | CH | 8.0 (1H,m), 6.9–7.5 (9H,m), 6.8 (2H,s), 5.8 (1H,t), 5.1 (2H,s), 2.7 (2H,m), 2.2 (2H,m). |
| 31 | 3-Br | Single bond | 1 | N | 8.0 (1H,m), 7.9 (2H,s + s), 6.9–7.5 (7H,m), 5.95 (1H, broad t), 5.05 (2H,s), 2.7 (2H,m), 1.8–2.5 (2H,m). |
| 32 | 4-Br | Single bond | 1 | N (HCl) | MP = 164–167° C. |
| 33 | 4-F | Single bond | 1 | H (HCl) | MP = 171–174° C. |
| 34 | 4-F | Single bond | 1 | N (HCl) | MP = 159–162° C. |
| 35 | 4-Br | Single bond | 1 | CH (HCl) | MP = 162–165° C. |
| 36 | 2-Br | Single bond | 1 | CH | 8.05 (1H,m), 6.8–7.5 (10H,m), 5.85 (1H,t), 5.22 (2H,s), 2.7 (2H,m), 2.2 (2H,m). |

TABLE I-continued

| Cpd No. | R | X | m | G | Melting Point (°C.) or NMR (delta, CDCl$_3$) |
|---|---|---|---|---|---|
| 37 | 2-Br | Single bond | 1 | N | 6.9–8.2 (10H,m), 6.0 (1H,t), 5.26 (2H,s), 1.8–2.9 (4H,m). |
| 38 | 2-Cl | Single bond | 1 | N (p-CH$_3$—C$_6$H$_4$—SO$_3$H) | MP = 60–65° C. |
| 39 | 2-Cl | Single bond | 1 | N (H$_2$SO$_4$) | MP = 104–110° C. |
| 40 | 3-CH$_3$ | Single bond | 1 | N | 8.05 (1H,m), 7.92 (1H,s), 7.86 (1H,s), 6.9–7.5 (7H,m), 5.98 (1H,t), 5.13 (2H,s), 2.7 (2H,m), 2.32 (3H,s). |
| 41 | 2-CH$_3$ | Single bond | 1 | N | 8.1 (1H,m), 7.9 (1H,s), 7.8 (1H,s), 6.9–7.5 (7H,m), 5.95 (1H,t), 5.2 (2H,s), 2.75 (2H,m), 2.35 (2H,m), 2.2 (3H,s). |
| 42 | 4-C(CH$_3$)$_3$ | Single bond | 1 | N | 8.14 (1H,m), 7.9 (2H,s + s), 7.0–7.5 (7H,m), 5.96 (1H, broad t), 5.15 (2H,s), 2.75 (2H,m), 2.35 (2H,m), 1.32 (9H,s). |
| 43 | 4-CN | Single bond | 1 | N | 8.1 (1H,m), 7.98 (2H,s), 7.94 (1H,s), 7.0–7.8 (7H,m), 6.0 (1H,t), 5.2 (2H,s), 2.75 (2H,m), 2.4 (2H,m). |
| 44 | 3-CN | Single bond | 1 | CH | 8.0 (1H,m), 7.0–7.6 (9H,m), 6.8 (1H,s), 5.82 (1h,t), 5.15 (2H,s), 2.7 (2H,m), 2.25 (2H,m). |
| 45 | 2-CH$_3$, 4-C(CH$_3$)$_3$ | S | 3 | N | 7.9–8.2 (2H,m), 7.0–7.4 (7H,m), 5.9 (1H, broad t), 4.25 (2H,t), 2.65–3.1 (4H,m), 2.4 (3H,s), 1.8–2.2 (4H,m), 1.3 (9H,s). |
| 46 | 4-NO$_2$ | Single bond | 1 | CH | 7.9–8.3 (3H,m), 6.85–7.7 (8H,m), 5.88 (1H,t), 5.24 (2H,s), 2.75 (2H,m), 2.3 (2H,m). |
| 47 | 4-CF$_3$ | Single bond | 1 | CH | 8.05 (1H,m), 6.8–7.7 (10H,m), 5.8 (1H,t), 5.2 (2H,s), 2.5–2.8 (2H,m) 2.0–2.5 (2H,m). |
| 48 | 4-OCH$_2$CH$_3$ | Single bond | 1 | CH | 8.05 (1H,m), 6.7–7.5 (10H,m), 5.72 (1H,t), 5.05 (2H,s), 3.94 (2H,q), 2.65 (2H,m), 2.15 (2H,m), 1.34 (3H,t). |
| 49 | 2-I | Single bond | 1 | CH (HCl) | 15.5 (1H, broad s), 9.2 (1H,s), 7.7–8.2 (2H,m), 6.8–7.5 (8H,m), 6.2 (1H, broad t), 5.2 (2H,s), 2.2–2.9 (4H,m). |
| a | 4-CO$_2$CH$_3$ | Single bond | 1 | N | 7.85–8.3 (3H,m), 7.1–7.5 (7H,m), 6.0 (1H,t), 5.3 (2H,s), 3.9 (3H,s), 2.75 (2H,m), 1.9–2.5 (2H,m). |
| a | 2-Cl, 6-F | Single bond | 1 | N (HCl) | MP = 153–158° C. |
| 50 | 4-CO$_2$CH$_3$ | Single bond | 1 | N | 7.85–8.3 (3H,m), 7.1–7.5 (7H,m), 6.0 (1H,t), 5.3 (2H,s), 3.9 (3H,s), 2.75 (2H,m), 1.9–2.5 (2H,m). |
| 51 | 2-Cl,6-F | Single bond | 1 | N (HCl) | MP = 153–158° C. |
| 52 | 2-I | Single bond | 1 | CH | 8.05 (1H,m), 6.8–7.9 (10H,m), 5.9 (1H,t), 5.22 (2H,s), 2.7 (2H,m), 2.25 (2H,m). |
| 53 | 4-Cl, 3-NO$_2$ | Single bond | 1 | CH | 8.0 (1H,m), 6.8–7.7 (9H,m), 5.84 (1H,t), 5.16 (2H,s), 2.75 (2H,m), 2.3 (2H,m). |
| 54 | 3-OCH$_3$ | Single bond | 1 | CH | 8.1 (1H,m), 6.7–7.5 (10H,m), 5.82 (1H,t), 5.12 (2H,s), 3.75 (3H,s), 2.7 (2H,m), 2.25 (2H,m), |
| 55 | 2-CN | Single bond | 1 | CH | 8.05 (1H,m), 6.8–7.7 (10H,m), 5.88 (1H,t), 5.32 (2H,s), 2.7 (2H,m), 2.25 (2H,m). |
| 56 | 2-Cl, 6-F | Single bond | 1 | N | 8.05 (1H,m), 7.88 (2H, broad s), 6.8–7.4 (6H,m), 5.9 (1H,t), 5.32 (2H,s), 2.75 (2H,m), 2.35 (2H,m). |
| 57 | [2,3]-CH=CH—CH=CH— | Single bond | 1 | N | 7.8–8.2 (3H,m), 6.9–7.6 (10H,m), 5.88 (1H,t), 5.58 (2H,s), 2.56 (2H,m), 1.8–2.5 (2H,m). |
| 58 | 2-CH$_3$ | Single bond | 1 | N (HNO$_3$) | MP = 60–65° C. |
| 59 | 4-CH$_3$ | Single bond | 1 | N | 8.1 (1H,m), 7.9 (1H,s), 7.85 (1H,s), 6.9–7.5 (7H,m), 5.95 (1H,t), 5.14 (2H,s), 2.75 (2H,m), 2.4 (2H,m), 2.32 (3H,s). |
| 60 | 4-OCH$_3$ | Single bond | 1 | N | 8.1 (1H,m), 7.9 (1H,s), 7.85 (1H,s), 6.9–7.4 (7H,m), 5.9 (1H,t), 5.06 (2H,s), 3.74 (3H,s), 2.7 (2H,m), 2.35 (2Hmn). |
| 61 | 4-Br | O | 2 | CH | 8.0 (1H,m), 6.6–7.8 (10H,m), 5.78 (1H,t), 4.4 (2H,m), 4.1 (2H,m), 2.7 (2H,m), |

TABLE I-continued

| Cpd No. | R | X | m | G | Melting Point (°C.) or NMR (delta, CDCl₃) |
|---|---|---|---|---|---|
| 62 | 2-CH₃, 4-C(CH₃)₃ | SO₂ | 3 | CH | 2.25 (2H,m).<br>7.9 (3H,m), 7.1–7.5 (6H,m),<br>5.78(1H, broad t), 4.2(2H,t),<br>2.6–3.4 (6H,m), 2.32 (3H,s), 2.25 (2H,m),<br>1.32 (9H,s). |
| 63 | 2-Cl, 4-Cl | Single bond | 1 | CH | 8.0 (1H,m), 6.8–7.6 (9H,m), 5.82 (1H,t),<br>5.24 (2H,s), 2.7 (2H,m), 2.2 (2H,m). |
| 64 | 2-Cl, 6-Cl | Single bond | 1 | CH | 8.1 (1H,m), 6.76–7.5 (9H,m), 5.8 (1H,t),<br>5.48 (2H,s), 2.7 (2H,m), 2.22 (2H,m). |
| 65 | 4-C₆H₅ | Single bond | 1 | N | 8.1 (1H,m), 7.9 (2H,s + s),<br>7.0–7.6 (12H,m), 5.95 (1H,t), 5.18 (2H,s),<br>2.65 (2H,m), 1.9–2.5 (2H,m). |
| 66 | 3-OC₆H₅ | Single bond | 1 | CH | 8.05 (1H,m), 6.7–7.5 (15H,m),<br>5.8 (1H,t), 5.1 (2H,s), 2.55–2.8 (2H,m),<br>1.9–2.3 (2H,m). |
| 67 | 4-OC₆H₅ | Single bond | 1 | N | 8.1 (1H,m), 7.9 (2H,s + s),<br>6.8–7.5 (12H,m), 5.92 (1H,t),<br>5.1 (2H,s), 2,75 (2H,m), 1.9–2.5 (2H,m). |
| 68 | 4-CF₃ | Single bond | 1 | CH (HCl) | 15.0 (1H, broad s), 9.5(1H,s),<br>8.0 (1H,m), 6.94–7.8 (9H,m),<br>6.2 (1H, broad t), 5.2 (2H,s),<br>2.2–2.9 (4H,m). |
| 69 | 3-Cl, 4-Cl | Single bond | 1 | N | 8.1 (1H,m), 7.98 (2H,s + s),<br>6.9–7.5 (6H,m), 5.98 (1H,t), 5.1 (2H,s),<br>2.7 (2H,m), 2.3 (2H,m). |
| 70 | 4-Cl | Single bond | 2 | N | 8.0 (1H,m), 7.9 (1H,s), 7.85 (1H,s),<br>6.9–7.4 (7H,m), 5.8 (1H,t), 4.35 (2H,t),<br>2.9 (2H,t), 2.7 (2H,m), 2.0–2.5 (2H,m). |
| 71 | 4-F | Single bond | 2 | N | 8.1 (1H,m), 7.9 (1H,s), 7.85 (1H,s),<br>6.8–7.3 (7H,m), 5.9 (1H,t), 4.35 (2H,t),<br>2.85 (2H,t), 2.65 (2H,m), 2.0–2.5–(2H,m). |
| 72 | 2-F | Single bond | 2 | N | 8.1 (1H,m), 7.95 (1H,s), 7.9 (1H,s),<br>6.9–7.4 (7H,m), 6.0 (1H,5), 4.4 (1H,t),<br>3.0 (2H,t), 2.6 (2H,t), 1.9–2.5 (2H,m). |
| 73 | 2-F | Single bond | 1 | CH | 8.0 (1H,m), 6.8–7.5 (10H,m), 5.7 (1H,m),<br>4.3 (2H,t), 3.4 (2H,t), 2.8 (2H,m),<br>2.5 (2H,m). |
| 74 | 4-F | Single bond | 2 | CH | 8.0 (2H,m), 6.7–7.5 (10H,m), 5.7<br>(1H,t), 4.3 (2H,t), 2.8–3.2 (2H,m),<br>2.6 (2H,m), 2.3 (2H,m). |
| 75 | 4-F | Single bond | 4 | N | 7.8–8.1 (3H,m), 6.8–7.4 (7H,m),<br>5.9 (1H,t), 4.1 (2H,t),<br>2.2–2.8 (6H,m), 1.8–2.2 (2H,m). |
| 76 | 4-Cl | Single bond | 3 | N | 8.1 (1H,m), 7.9 (2H,s + s),<br>5.9 (1H,t), 4.2 (2H,t),<br>2.3–2.8 (6H,m), 1.8–2.1 (2H,m). |
| 77 | 4-Cl | Single bond | 3 | CH | 8.1 (1H,m), 6.8–7.5 (10H,m),<br>5.7 (1H,5), 4.15 (2H,t),<br>2.2–2.8 (6H,m), 1.8–2.2 (2H,m). |
| 78 | 4-Br | Single bond | 2 | CH | 8.1 (2H,m), 6.8–7.5 (10H,m), 5.75 (H,t),<br>4.35 (2H,t), 2.85 (2H,t), 2.7 (2H,m),<br>2.25 (2H,m). |
| 79 | 4-Br | Single bond | 2 | N | 8.0 (1H,m), 7.9 (1H,s), 7.8 (1H,s),<br>7.8 (1H,s), 6.0–7.4 (7H,m), 5.8 (1H,t),<br>4.2 (2H,t), 2.8 (2H,t), 2.6 (1H,m),<br>1.9–2.3 (2H,m). |
| 80 | 2-Cl | Single bond | 3 | N | 8.1 (1H,m), 7.95 (1H,s), 7.9 (1H,s),<br>7.9 (1H,s), 6.9–7.4 (7H,m), 5.9 (1H,t),<br>4.2 (2H,t), 2.2–2.8 (6H,m),<br>1.8–2.1 (1H,m). |
| 81 | 2-Cl | Single bond | 3 | CH | 8.0 (1H,m), 6.8–7.4 (10H,m), 5.8 (1H,t)<br>4.2 (2H,t), 2.3–2.8 (6H,m),<br>1.8–2.1 (2H,m). |

EXAMPLE 12

Preparation of Fungicidal and Plant Regulant Compositions

The compounds prepared in Examples 3–10 (Compound Nos. 1–81) were formed into compositions. This was accomplished by dissolving 0.3 g. of each of the compounds in 10 ml. of acetone or other suitable solvent. Each of these solutions were treated with 1 to 2 drops of an emulsifying agent, such as Triton¶X-100, and water was added to form an emulsion. The degree of dilution with water was dictated by the desired concentration of the composition. The greater the quantity of water added the lower was the concentration of the composition, reported in milligrams per liter (mg/l).

EXAMPLE 13

Control of Powdery Mildew Fungus (Systemic Root Uptake)

Each of the compounds prepared in accordance with Examples 3–10, Compound Nos. 1–81, were tested to evaluate their effectiveness in preventing or controlling powdery mildew disease of barley caused by the fungus *Erysiphe graminis* and powdery mildew disease of cucumber caused by the fungus, *Erysiphe cichoracearum*. This prevention or control capability was tested by utilizing the compounds of the present invention to control these diseases by systemic root uptake.

To accomplish this task, pots (4×4×3.5 inches) containing 10 plants of barley (Variety "Herta") and cucumber (Variety "Marketmore 70") were grown to age 6 days and 10 days, respectively. Upon reaching these ages, 45 ml. of emulsion compositions formed in accordance with Example 12 were added to each pot. That is, 73 pots were treated with emulsion compositions of the 73 compounds prepared in accordance with Examples 3 to 10. The 45 ml. compositions saturated the soil without significant loss through drainage into the saucers below the pots. In addition, a number of pots containing the same barley and cucumber plants were left untreated. These pots were used as controls.

Twenty-four hours after the treatment with the compositions of the present invention, both the barley and cucumber plants in all the pots, those treated and those untreated, were inoculated with powdery mildew fungus. This was accomplished by tapping leaves of previously infected barley and cucumber plants over the treated and untreated pots containing the barley and cumber plants, respectively, to distribute spores of the fungus over the plants tested.

Six days after inoculation, disease control was evaluated on a 0 to 6 rating scale. A 0 rating was assigned when no disease was evidenced and a 6 rating was given for severe disease. Intermediate ratings were assigned depending on the degree of disease. Percent control was computed by comparing the ratings for the treated and untreated plants.

The results of this example, that is, the percent control for each of the compounds tested is reported in Table II. The results of the powdery mildew disease control of barley is reported under the title "BMS 250". The control of cucumber powdery mildew is similarly reported under the title of "CMS 250." It is noted that Table II appears after Example 17.

EXAMPLE 14

Control of Powdery Mildew in Barley by Foliar Application

Eight plants of "Larker" variety barley were planted in a pot. The number of pots were sufficient to accommodate testing in duplicate or triplicate pots for each of the 48 compounds tabulated in Table I. This number included a duplicate number of pots which acted as controls as will be discussed below.

Each of the compounds tabulated in Table 1 were tested by being sprayed onto the plants as compositions, prepared in accordance with Example 12, at a emulsion composition concentration of 1,000 ppm. Compositions of each compound were sprayed on two or three pots. An equal number of pots were unsprayed and thus acted as controls. That is for each pot sprayed an unsprayed pot was utilized as a control.

After the leaves of the sprayed pots were dried, they and the unsprayed control pots were placed in a greenhouse maintained at 21° C. All the pots were there inoculated with barley powdery mildew fungus, *Erysiphe graminis*. This inoculation was accomplished by distributing spores of the fungus over the leaves to be tested from plants which had previously been infected with the mildew disease.

Five days after inoculation, the plants were evaluated and assigned a disease rating of 0 to 6 as described in Example 13. Again, percent control was computed by comparing the treatment scores with the scores of the untreated controls. The results of these tests are summarized in Table II under the title "BMP 1000."

EXAMPLE 15

Control of Rice Blast Disease by Foliar Treatment

Five Bellemont rice plants were grown in a plurality of pots. The number of pots with planted rice plants were sufficient to test the compositions of all 73 compounds listed in Table I as well as controls therefor, the number of controls equal to the number of pots treated with each compound.

Three to four weeks after planting, the rice plants were sprayed with compositions of the compounds of this invention, prepared in accordance with Example 12. The concentration of each composition was 1,000 mg/l. An equal number of pots, also containing five rice plants per pot, remained unsprayed.

Sprayed and unsprayed pots of the plant were inoculated with spores of the rice blast fungus, *Pyricularia oryzae*. This inoculation was accomplished by preparing inoculum containing 20,000 to 30,000 spores per millilitre. The inoculum so prepared was sprayed on the plants with 1 to 2 drops of Tween [trademark]20 surfactant (ethoxylated sorbitan monolaurate) to insure proper wetting of the inoculum onto the plant leaves.

The plants were incubated in a controlled chamber at a humidity of 99% and a temperature of 21° C. for about 24 hours to allow infection to occur. The plants, after 24 hours in the control chamber, were transferred to a greenhouse for six days to permit disease development to occur. Disease was manifested by blast lesions on the leaves. Disease control was calculated by either counting lesions, if infection was moderate, or evaluating by the 0 to 6 rating system defined in Example 13. Of course, the evaluation system used in rating any of the compounds of the present invention was also utilized in evaluating its control. The results of this test are also tabulated in Table II under the title "RCB 1000."

EXAMPLE 16

Control of Bean Rust Fungus Eradicant Test

Pots were planted with two pinto bean plants, *P. vulgaris* each, susceptible to rust disease. When the plants were 7 days old, at the primary leaf stage of growth, they were all sprayed with a suspension containing 20,000 spores of the bean rust fungus, *Uromyces phaseoli*, per ml. All the pots containing the plants were then incubated in a controlled environmental chamber, maintained at 99% humidity and 21° C., for 24 hours to allow infection to occur. The plants were then removed from the incubator and allowed to dry. Two days after inoculation the infected plants were sprayed with compositions formed from the compounds of this invention, set forth in Example 12, at a dosage of 1,000 mg/l. A number of infected plants were not sprayed and acted as controls. All of the sprayed and unsprayed plants were then placed in a greenhouse at 21° C. for five days to allow any disease present to be expressed.

All the plants sprayed with the spore suspension were assessed for disease using the 0 to 6 rating system described in Example 13. Control of disease was determined by comparing treated plants with the untreated controls. The control of disease, expressed as percent reduction of disease, is included in Table III under the title "BRE 1000."

EXAMPLE 17

Control of Nine Fungus Species

Compounds listed in Table I were solubilized in acetone at a concentration of 500 mg/l for all fungus species. Filter paper discs, each 11 mm. diameter, were dipped in each of the test solutions. The discs were allowed to air dry to drive off the acetone solvent. A number of discs were untreated to provide controls.

The treated and untreated discs were then placed on agar plates and 8 fungus species: *Alternaria solani* (ALT), *Botrytis cinerea* (BOT), *Fusarium oxysporum* (FUS) *Helminthosporium maydis* (HMAY) *Phytophthora infestans* (PHY), *Sclerotinia sclerotiorum* (SCM) and *Sclerotium rolfsii* (SCO) were added to the center of each test disc in the form of a culture plug with the fungus mat in contact with the treated paper of the test disc. Two drops of a ninth fungi species, *Cercospora arachidicola* (CER), were added as a spore suspension 20,000 spores/ml) to the chemically treated test disc, rather than a mycelial culture plug. The plates were incubated at 29° C. in an oven and then the eight fungus species were evaluated by measuring the radius from the center of the fungus colony of the treated disc compared to the radius from the center of the fungus colony of the untreated discs.

Percent growth inhibition of each of the compounds tested was determined as a function of the difference between the radii of the treated and untreated discs for the eight fungus species.

In the case of the *Cercospora arachidicola* (CER) fungi, scoring was done on a numerical basis as follows:

100=Complete inhibition of germination and growth.

50=Partial inhibition of growth or, early complete inhibition but later growth begins.

0=No inhibition of growth.

TABLE II

Fungicidal Activity

| Cpd. No. | ALT 500 (Ex17) | RMS 250 (Ex13) | BOT 500 (Ex17) | BRE 1000 (Ex16) | CER 500 (Ex17) | CMS 250 (Ex13) | FUS 500 (Ex17) | HMAY 500 (Ex17) | PHY 500 (Ex17) | PMP 1000 (Ex17) | RCB 1000 (Ex15) | SCM 500 (Ex17) | SCO 500 (Ex17) | BMP 1000 (Ex14) |
|---|---|---|---|---|---|---|---|---|---|---|---|---|---|---|
| 1 | 65 | 90 | 50 | 0 | 50 | 20 | 40 | 0 | 85 | 0 | 65 | 25 | 0 | 90 |
| 2 | 55 | 15 | 30 | 0 | 100 | 0 | 50 | 55 | 75 | 0 | 95 | 10 | 0 | 90 |
| 3 | 76 | 15 | 0 | 95 | 100 | 40 | 40 | 80 | 65 | 0 | 95 | 29 | 65 | 100 |
| 4 | 100 | 40 | 100 | 25 | 100 | 20 | 85 | 100 | 100 | 50 | — | 20 | 40 | — |
| 5 | 75 | 0 | 75 | 0 | 100 | 20 | 100 | 100 | 80 | 0 | 15 | 5 | 60 | 15 |
| 6 | 35 | 0 | 85 | 75 | 0 | 0 | 50 | 35 | 30 | 80 | 100 | 30 | 10 | 100 |
| 7 | 50 | 0 | 85 | 80 | 100 | 0 | 50 | 50 | 75 | 50 | 100 | 35 | 0 | 100 |
| 8 | 35 | 0 | 100 | 0 | 100 | 0 | 65 | 55 | 100 | 0 | 100 | 35 | 0 | 100 |
| 9 | 95 | 0 | 100 | 0 | 100 | 0 | 75 | 100 | 100 | 0 | 100 | 65 | 75 | 100 |
| 10 | 100 | 0 | 100 | 50 | 100 | 0 | 100 | 100 | 100 | 90 | 100 | 35 | 0 | 90 |
| 11 | 100 | 0 | 100 | 60 | 100 | 0 | 100 | 100 | 100 | 75 | 100 | 35 | 0 | 100 |
| 12 | 95 | 35 | 55 | 96 | 100 | 50 | 85 | 100 | 100 | 0 | — | 15 | 0 | — |
| 13 | 85 | 0 | 50 | 100 | 100 | 50 | 80 | 85 | 100 | 50 | — | 0 | 0 | — |
| 14 | 75 | 15 | 55 | 100 | 100 | 0 | 80 | 80 | 100 | 50 | — | 25 | 0 | — |
| 15 | 65 | 15 | 75 | 50 | 100 | 75 | 90 | 85 | 100 | 0 | 50 | 0 | 0 | 85 |
| 16 | 65 | 15 | 50 | 90 | 0 | 50 | 50 | 50 | 75 | 0 | — | 15 | 0 | — |
| 17 | 55 | 15 | 50 | 0 | 0 | 20 | 0 | 0 | 75 | 50 | — | 0 | 0 | — |
| 18 | 65 | 15 | 35 | 0 | 0 | 0 | 20 | 50 | 75 | 75 | 50 | 55 | 35 | 100 |
| 19 | 10 | 15 | 0 | 0 | 0 | 25 | 15 | 20 | 50 | 75 | 65 | 0 | 0 | 100 |
| 20 | 0 | 35 | 25 | 0 | 0 | 15 | 0 | 0 | 50 | 75 | 65 | 0 | 0 | 100 |
| 21 | 20 | 0 | 0 | 50 | 0 | 0 | 15 | 0 | 25 | 100 | 15 | 0 | 0 | 40 |
| 22 | 95 | 0 | 20 | 25 | 100 | 90 | 90 | 100 | 100 | 75 | 100 | 0 | 65 | 100 |
| 23 | 40 | 0 | 0 | 40 | 50 | 15 | 60 | 25 | 55 | 100 | 65 | 45 | 35 | 100 |
| 24 | 65 | 20 | 50 | 30 | 100 | 35 | 90 | 90 | 100 | 95 | 65 | 0 | 0 | 100 |
| 25 | 55 | 0 | 0 | 15 | 0 | 15 | 60 | 20 | 75 | 100 | 100 | 25 | 15 | 100 |
| 26 | 100 | 0 | 25 | 50 | 100 | 15 | 85 | 100 | 100 | 95 | 100 | 0 | 15 | 100 |
| 27 | 40 | 0 | 0 | 70 | 50 | 35 | 60 | 40 | 55 | 100 | 100 | 35 | 45 | 100 |
| 28 | 85 | 20 | 100 | 35 | 100 | 0 | 50 | 90 | 100 | 95 | 100 | 40 | 100 | 100 |
| 29 | 55 | 0 | 0 | 40 | 0 | 0 | 85 | 35 | 75 | 100 | 100 | 25 | 10 | 100 |
| 30 | 100 | 0 | 100 | 35 | 100 | 15 | 60 | 90 | 100 | 90 | 100 | 10 | 35 | 100 |
| 31 | 40 | 0 | 10 | 10 | 50 | 0 | 60 | 35 | 80 | 100 | 100 | 0 | 0 | 100 |
| 32 | 40 | 0 | 0 | 25 | 0 | 15 | 60 | 35 | 45 | 100 | 65 | 25 | 0 | 100 |
| 33 | 75 | 0 | 25 | 90 | 100 | 35 | 100 | 100 | 100 | 90 | 100 | 10 | 40 | 100 |
| 34 | 55 | 0 | 0 | 85 | 0 | 15 | 50 | 50 | 80 | 95 | 50 | 25 | 35 | 100 |
| 35 | 100 | 40 | 100 | 90 | 100 | 0 | 100 | 100 | 100 | 80 | 100 | 45 | 10 | 100 |
| 36 | 100 | 0 | 50 | 75 | 100 | 15 | 100 | 100 | 100 | 95 | 100 | 0 | 35 | 100 |
| 37 | 65 | 0 | 35 | 35 | 100 | 15 | 50 | 35 | 55 | 95 | 100 | 0 | 100 | 100 |
| 38 | 80 | 0 | 0 | 90 | 0 | 60 | 55 | 45 | 100 | 95 | 100 | 0 | 0 | 100 |
| 39 | 40 | 0 | 0 | 95 | 100 | 0 | 15 | 50 | 100 | 100 | 100 | 35 | 0 | 100 |
| 40 | 45 | 0 | 75 | 0 | 0 | 20 | 60 | 80 | 75 | 0 | 90 | 0 | 60 | 100 |
| 41 | 75 | 35 | 90 | 0 | 50 | 40 | 45 | 55 | 80 | 0 | 90 | 0 | 90 | 100 |
| 42 | 5 | 0 | 25 | 0 | 0 | 0 | 30 | 25 | 70 | 75 | 90 | 0 | 35 | 100 |
| 43 | 60 | 50 | 100 | 0 | 0 | 20 | 55 | 80 | 90 | 100 | 90 | 0 | 15 | 100 |
| 44 | 90 | 35 | 90 | 0 | 50 | 40 | 80 | 90 | 100 | 0 | 100 | 40 | 20 | 100 |
| 45 | 15 | 15 | 0 | 0 | 0 | 0 | 0 | 0 | 0 | 0 | 90 | 40 | 15 | 90 |
| 46 | 90 | 0 | 90 | 0 | 100 | 0 | 90 | 95 | 90 | 0 | 100 | 10 | 55 | 100 |
| 47 | 95 | 0 | 100 | 0 | 100 | 0 | 90 | 100 | 100 | 0 | 100 | 30 | 65 | 100 |
| 48 | 70 | 15 | 100 | 0 | 100 | 15 | 90 | 75 | 70 | 0 | 40 | 10 | 70 | 50 |
| 49 | 100 | 0 | 0 | 100 | 100 | 15 | 90 | 85 | 100 | 0 | 100 | 10 | 45 | 100 |
| 50 | 45 | 0 | 10 | 0 | 0 | 15 | 50 | 25 | 40 | 0 | 0 | 30 | 0 | 50 |
| 51 | 70 | 65 | 70 | 15 | 0 | 15 | 80 | 25 | 60 | 35 | 100 | 0 | 20 | 100 |
| 52 | 95 | 33 | 100 | 0 | 100 | 35 | 90 | 100 | 100 | 0 | 80 | 20 | 45 | 100 |
| 53 | 100 | 15 | 100 | 0 | 100 | 15 | 100 | 100 | 75 | 0 | 100 | 0 | 25 | 100 |

TABLE II-continued

| | | | | | | Fungicidal Activity | | | | | | | | |
|---|---|---|---|---|---|---|---|---|---|---|---|---|---|---|
| Cpd. No. | ALT 500 (Ex17) | RMS 250 (Ex13) | BOT 500 (Ex17) | BRE 1000 (Ex16) | CER 500 (Ex17) | CMS 250 (Ex13) | FUS 500 (Ex17) | HMAY 500 (Ex17) | PHY 500 (Ex17) | PMP 1000 (Ex17) | RCB 1000 (Ex15) | SCM 500 (Ex17) | SCO 500 (Ex17) | BMP 1000 (Ex14) |
| 54 | 70 | 0 | 100 | 0 | 100 | 0 | 80 | 100 | 25 | 0 | 85 | 0 | 25 | 100 |
| 55 | 50 | 0 | 50 | 0 | 100 | 15 | 50 | 85 | 25 | 0 | 35 | 0 | 0 | 85 |
| 56 | 80 | 35 | 100 | 0 | 100 | 15 | 50 | 10 | 50 | 0 | 100 | 0 | 25 | 100 |
| 57 | 50 | 15 | 60 | 0 | 0 | 0 | 10 | 10 | 25 | 0 | 35 | 0 | 0 | 85 |
| 58 | 50 | 0 | 10 | 0 | 0 | 15 | 35 | 10 | 25 | 0 | 40 | 0 | 25 | 100 |
| 59 | 50 | 35 | 0 | 0 | 0 | 15 | 50 | 55 | 25 | 0 | 35 | 45 | 50 | 100 |
| 60 | 50 | 0 | 25 | 0 | 0 | 15 | 40 | 45 | 25 | 0 | 85 | 25 | 0 | 65 |
| 61 | 60 | 0 | 75 | 0 | 50 | 35 | 75 | 100 | 25 | 0 | 65 | 0 | 20 | 35 |
| 62 | 25 | 0 | 50 | 0 | 0 | 15 | 0 | 55 | 0 | 0 | 65 | 0 | 0 | 100 |
| 63 | 100 | 35 | 100 | 0 | 100 | 35 | 85 | 75 | 100 | 0 | 90 | 0 | 45 | 100 |
| 64 | 100 | 15 | 100 | 0 | 100 | 0 | 85 | 45 | 100 | 0 | 15 | 0 | 50 | 100 |
| 65 | 60 | 35 | 75 | 0 | 0 | 15 | 35 | 35 | 60 | 0 | 0 | 0 | 0 | — |
| 66 | 80 | 35 | 100 | 0 | 100 | 15 | 75 | 65 | 100 | 0 | 0 | 35 | 60 | — |
| 67 | 60 | 15 | 9 | 0 | 0 | 15 | 40 | 65 | 65 | 0 | 0 | 10 | 40 | 90 |
| 68 | 85 | 0 | 30 | 0 | 100 | 0 | 85 | 100 | 100 | 0 | 100 | 25 | 10 | 100 |
| 69 | 75 | 50 | 80 | 70 | 0 | 15 | 60 | 10 | 100 | 50 | 100 | 10 | 30 | 100 |
| 70 | 75 | 15 | 15 | 0 | 100 | 0 | 5 | 100 | 55 | 100 | 0 | 65 | 0 | 90 |
| 71 | 65 | 15 | 70 | 0 | 50 | 0 | 0 | 100 | 25 | 90 | 0 | 90 | 25 | — |
| 72 | 55 | 0 | 95 | 0 | 50 | 0 | 5 | 100 | 15 | 100 | 0 | 90 | 100 | — |
| 73 | 15 | 35 | 75 | 0 | 100 | 20 | 0 | 75 | 15 | 0 | 0 | 100 | 40 | — |
| 74 | 100 | 0 | 40 | 0 | 100 | 15 | 55 | 100 | 100 | 0 | 0 | 20 | 100 | 0 |
| 75 | 0 | 0 | 10 | 0 | 0 | 0 | 0 | 0 | 0 | 50 | 85 | 0 | 40 | 100 |
| 76 | 10 | 0 | 0 | 0 | 0 | 0 | 0 | 0 | 0 | 0 | 90 | 0 | 0 | 90 |
| 77 | 60 | — | 0 | 0 | 100 | — | 65 | 100 | 75 | — | — | 40 | 40 | — |
| 78 | 100 | 0 | 40 | 100 | 100 | 0 | 100 | 100 | 100 | 35 | 100 | 0 | 5 | 100 |
| 79 | 55 | 0 | 0 | 100 | 100 | 35 | 0 | 100 | 80 | 100 | 75 | 0 | 0 | 100 |
| 80 | 20 | 0 | 35 | 0 | 0 | 0 | 0 | 50 | 35 | 0 | 90 | 0 | 0 | 90 |
| 81 | 60 | 0 | 75 | 0 | 0 | 100 | 90 | 100 | 80 | 75 | 100 | 70 | 0 | 90 |

Example 18

Growth Regulation of Soybean, Cotton, Bean and Barley Plants

Aqueous compositions of Compound Nos. 1–22, 24–37, 39–42, 44, 52, 61, 65 and 70–72 were prepared in accordance with the procedure set forth in Example 12. In particular, these compositions were prepared in concentrations of 1,000 mg/l and 3,000 mg/l from 450 mg. of the compound dissolved or dispersed in 10 ml. distilled water or an organic solvent, usually acetone, to which 20 mg. of an emulsifying agent, usually ethoxylated sorbitan monolaurate (Tween [trademark of ICI, America] 20), was added. The solution or dispersion was diluted to 150 ml. with distilled water, producing a 3,000 mg/l aqueous composition. By appropriate further dilution with distilled water, a 1,000 mg/l aqueous composition was prepared.

The compositions, prepared in accordance with the above procedure, were atomized with a DeVilbiss [trademark] No. 152 sprayer onto the foliage of soybean plants (*Glycine max* (L.) Merr. cv. Williams, 2 weeks old), cotton plants (*Gossypium hirsutum* L. cv. Stoneville 213, 3 to 4 weeks old), bean plants (*Phaseolus vulgaris* L. cv. Pinto III, 2 weeks old) and barley plants (*Hordeum vulgare* L. cv. Herta, 1 week old). Spraying continued until the foliage was wetted to the drip point. After 1 to 3 weeks, depending on the plant species, the plants were evaluated for retardation of vegetative growth, $$\text{Per Cent Growth Control} = \frac{\text{(Height of Control)} - \text{(Height of Treated)}}{\text{(Height of Control)}} \times 100$$

The results of this test are summarized in Table III.

TABLE III

| | Percent Growth Retardation | | | |
|---|---|---|---|---|
| Cpd. No. | Bean (1000 ppm) | Barley (3000 ppm) | Cotton (3000 ppm,) | Soybean (3000 ppm) |
| 1 | 0 | 0 | 50 | 90 |
| 2 | 0 | 0 | 20 | 0 |
| 3 | 0 | 0 | 50 | 50 |
| 4 | 40 | 0 | 75 | 0 |
| 5 | 0 | 0 | 30 | 0 |
| 6 | 50 | 0 | 100 | 50 |
| 7 | 0 | 0 | 90 | 90 |
| 8 | 0 | 0 | 95 | 30 |
| 9 | 0 | 0 | 30 | 0 |
| 10 | 0 | 0 | 100 | 20 |
| 11 | 0 | 0 | 100 | 0 |
| 12 | 80 | 0 | NT | 0 |
| 13 | 90 | 0 | NT | 0 |
| 14 | 50 | 0 | NT | 0 |
| 15 | 50 | 0 | NT | °75 |
| 16 | 50 | 0 | NT | 0 |
| 17 | 80 | 0 | NT | 100 |
| 18 | 30 | 0 | NT | 0 |
| 19 | 90 | 0 | NT | 0 |
| 20 | 20 | 0 | NT | 0 |
| 21 | 95 | 0 | NT | 100 |
| 22 | 20 | 0 | NT | 0 |
| 24 | 20 | 0 | NT | 0 |
| 25 | 20 | 0 | NT | 0 |
| 26 | 20 | 0 | NT | 0 |
| 27 | 15 | 0 | NT | 0 |
| 28 | 30 | 0 | NT | 0 |
| 29 | 90 | 0 | NT | 0 |
| 30 | 50 | 0 | NT | 0 |
| 31 | 30 | 50 | NT | 0 |
| 32 | 90 | 30 | NT | 0 |
| 33 | 50 | 0 | NT | 0 |
| 34 | 20 | 0 | NT | 0 |
| 35 | 30 | 0 | NT | 0 |
| 36 | 20 | 0 | NT | 0 |
| 37 | 15 | 40 | NT | 0 |
| 39 | 20 | 30 | NT | 0 |
| 40 | 20 | 0 | NT | 0 |
| 41 | 20 | 0 | NT | 0 |
| 42 | 90 | 0 | NT | 0 |
| 44 | 20 | 0 | NT | 0 |
| 52 | 0 | 0 | NT | 20 |

TABLE III-continued

| | Percent Growth Retardation | | | |
|---|---|---|---|---|
| Cpd. No. | Bean (1000 ppm) | Barley (3000 ppm) | Cotton (3000 ppm,) | Soybean (3000 ppm) |
| 61 | 0 | 0 | NT | 20 |
| 65 | 0 | 0 | NT | 75 |
| 70 | 90 | 0 | NT | 0 |
| 71 | 50 | 0 | NT | 100 |
| 72 | 90 | 0 | NT | 100 |

NT = Not Tested

The above embodiments and examples are given to illustrate the scope and spirit of the instant invention. These embodiments and examples will make apparent, to those skilled in the art, other embodiments and examples. These other embodiments and examples are within the contemplation of the present invention. Therefore, this invention should be limited only by the appended claims.

What is claimed is:

1. A compound having the structural formula (I)

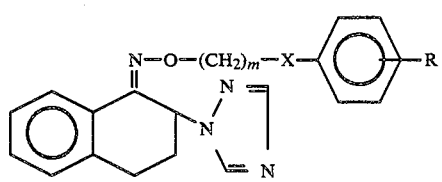

(I)

in which:

R is a substituent or a group of substituents representing halogen, low alkyl of 1 to 6 carbon atoms, phenyl, phenoxy, naphthyl, nitro, cyano, low alkoxy, alkoxycarbonyl, or trifluoromethyl;

X is single bond, oxygen, sulfur or sulfonyl:

m is an integer from 1 to 4.

2. A compound according to claim 1 wherein

R is a substituent or a group of substituents representing halogen, nitro, cyano, low alkoxy or trifluoromethyl:

X is a single bond:

m is an integer from 1 to 4.

3. A process for controlling phytopathogenic fungic comprising applying a fungicidally effective amount of the compound of claim 1 to the locus under attack by said fungi.

4. A process for controlling phytopathogenic fungi comprising applying the compound of claim 1, at a concentration of 10 ppm to 500 ppm, to the soil in which said plants to be protected from phytopathogenic fungi are grown.

5. A process for controlling phytopathogenic fungi in a plurality of plants growing in soil comprising applying the compound of claim 1 as a coating to seeds of plants to be protected from said phytopathogenic fungi at a coating concentration of 5 to 75 grams of the compound of claim 1 per 100 kg. of said seed.

6. A process for regulating plant growth comprising applying a plant growth regulant effective amount of the compound of claim 1 to the plant whose growth is to be regulated.

7. A fungicidal composition comprising a fungicidally effective amount of the compound of claim 1 and a carrier therefor.

8. A plant growth regulant composition comprising a plant growth regulant effective amount of the compound of claim 1 and a carrier therefor.

* * * * *